(12) United States Patent
Gayton

(10) Patent No.: US 7,056,330 B2
(45) Date of Patent: Jun. 6, 2006

(54) METHOD FOR APPLYING TISSUE FASTENER

(75) Inventor: John F. Gayton, Bettendorf, IA (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 335 days.

(21) Appl. No.: 10/440,958

(22) Filed: May 16, 2003

(65) Prior Publication Data

US 2003/0233105 A1 Dec. 18, 2003

Related U.S. Application Data

(60) Provisional application No. 60/385,248, filed on May 31, 2002.

(51) Int. Cl.
*A61B 17/08* (2006.01)
*A61D 1/00* (2006.01)

(52) U.S. Cl. .................. 606/219; 606/139; 606/142; 606/143; 606/151; 606/75; 227/175.1

(58) Field of Classification Search .................. 606/60, 606/75, 139, 142, 143, 151, 155, 219, 220, 606/221; 227/175.1

See application file for complete search history.

(56) References Cited

U.S. PATENT DOCUMENTS

| | | | | |
|---|---|---|---|---|
| 4,317,451 A | * | 3/1982 | Cerwin et al. | ............... 606/220 |
| 4,802,478 A | * | 2/1989 | Powell | ............... 606/138 |
| 4,850,355 A | | 7/1989 | Brooks et al. | |
| 4,874,122 A | * | 10/1989 | Froelich et al. | ............... 227/19 |
| 5,222,961 A | | 6/1993 | Nakao et al. | |
| 5,236,440 A | * | 8/1993 | Hlavacek | ............... 606/219 |
| 5,423,835 A | | 6/1995 | Green et al. | |
| 5,425,489 A | * | 6/1995 | Shichman et al. | ............... 227/108 |
| 5,695,524 A | * | 12/1997 | Kelley et al. | ............... 606/219 |
| 5,700,271 A | | 12/1997 | Whitfield et al. | |
| 5,725,554 A | * | 3/1998 | Simon et al. | ............... 606/219 |
| 5,833,696 A | | 11/1998 | Whitfield et al. | |
| 6,059,799 A | | 5/2000 | Aranyi et al. | |
| 6,277,131 B1 | | 8/2001 | Kalikow | |
| 6,306,149 B1 | | 10/2001 | Meade | |

FOREIGN PATENT DOCUMENTS

| EP | 0769274 B1 | 3/2003 |
|---|---|---|
| EP | 1317905 A2 | 6/2003 |

OTHER PUBLICATIONS

EPO Search Report dated Aug. 5, 2003, for EPO Appl. No. 03 25 3396.

* cited by examiner

*Primary Examiner*—Julian M. Moo
*Assistant Examiner*—Michael Mendoza

(57) ABSTRACT

A method for applying a surgical fastener including the steps of providing a fastener applier having an elongated shaft with at least one fastener located within the elongated shaft. The fastener has a pair of bosses extending laterally therefrom. The fastener has an open and closed position. The method further includes the step of inserting the distal end of the shaft into a target location within a body of a patient. Thereafter, the method includes applying at least one fastener within a body of a patient. This step involves the steps of advancing the at least one fastener within the shaft so it is adjacent the distal end, placing the fastener in contact with tissue, and closing the fastener by moving the bosses away from each other as the fastener is advanced distally.

1 Claim, 10 Drawing Sheets

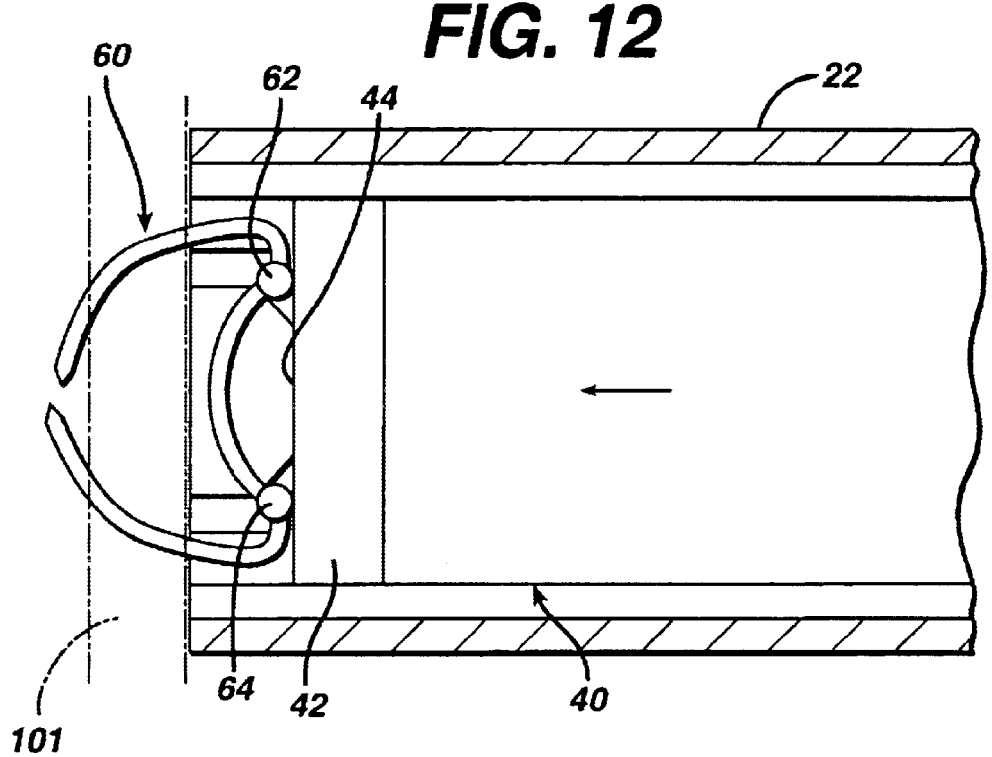
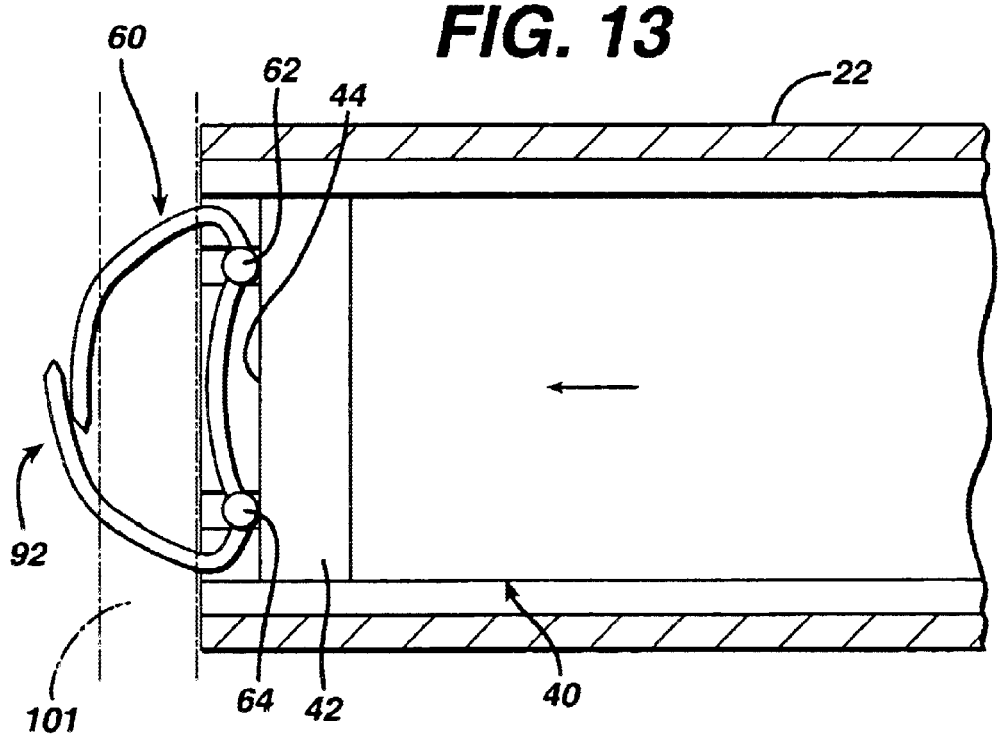

METHOD FOR APPLYING TISSUE FASTENER

CROSS-REFERENCE TO RELATED APPLICATIONS

This application claims the benefit of provisional application Ser. No. 60/385,248 filed May 31, 2002.

FIELD OF THE INVENTION

This invention generally relates to surgical methods, and more particularly, the invention relates to surgical methods for placing fasteners in tissue.

BACKGROUND OF THE INVENTION

In recent years, there have been many advances in endoscopic and laparoscopic surgical procedures. In these procedures, a surgeon makes an incision at the desired location where the surgical procedure is to be performed. Typically, a trocar is then inserted into the incision made by the surgeon. By applying pressure against the proximal end of the trocar, the obturator is forced through the tissue until it enters a target location, such as the abdominal cavity or any other desired hollow viscus of the body. The cannula is inserted through the perforation made by the obturator and the obturator is withdrawn, leaving the cannula as an accessway to the abdominal cavity. If desired, a pressurizing gas such as, for example, carbon dioxide can be pumped through the cannula of the trocar to inflate the abdomen or hollow viscus of the body. Then, any number of surgical instruments such as, for example, a tissue fastening instrument can be inserted through the cannula of the trocar to perform the surgical procedure.

One such tissue fastening instrument inserted through the cannula during a surgical procedure is the surgical stapler. Surgical staplers are employed by the surgeon during the procedure to sequentially or simultaneously apply one or more surgical fasteners such as, for example, staples or two-part fasteners to body tissue for the purpose of joining segments of body tissue together. An example of a surgical stapler is disclosed in U.S. Pat. No. 5,725,554 issued to Simon et al. A surgical stapler and staple is described for joining together tissue of a patient. The surgical stapler has a long endoscopic arm, a stapling actuation mechanism located at the end of the endoscopic arm, and a handle with a trigger. The staple, which is a rounded M-shape, has a circular cross-section with a flat surface on the lower side. The operation of the trigger causes a linear force to travel through the length of the arm to the stapling actuation mechanism, which forms the staple to fasten tissue. One drawback of the design of this surgical stapler and staple is that the long endoscopic arm has a large cross-section, which requires a larger access port and larger incision to reach the surgical site.

Another such tissue fastening instrument inserted through the cannula during a surgical procedure is the clip applier. Clip appliers are employed by the surgeon during the procedure to sequentially or simultaneously apply one or more clips to body tissue for the purpose of pinching vessels. An example of a clip applier is disclosed in U.S. Pat. No. 5,843,097 issued to Mayenberger et al. A surgical applicator for U-shaped clips is described comprising a handle, a tubular shaft adjoining the handle, a forceps-type applicator tool at the free end of the tubular shaft, a clip magazine in the tubular shaft, a closing mechanism comprising jaws at the distal end of the tubular shaft, and an advancing mechanism arranged in the tubular shaft. The advancing mechanism pushes a clip into the jaws of the closing mechanism. When the handle is actuated, the jaws of the closing mechanism pinch the clip around the vessel. One drawback of the design of this surgical applicator and its U-shaped clip is that the tubular shaft has a large cross-section, which requires a larger access port and larger incision to reach the surgical site.

In minimally invasive surgery, in particular, endoscopic or laparoscopic surgery, it has become desirable to provide smaller instruments capable of reaching surgical sites through smaller access ports, yet still providing the ability to deliver relatively large staples and clips therethrough. Smaller incisions cause less damage in accessing the surgical site and the access wounds from such incisions heal faster. The presently known surgical fastening devices such as, for example, clip appliers and surgical staplers all exhibit the drawback of having an instrument shaft with a large cross-section, which is dictated, in general, by the size of the fastener as it is passed therethrough. Having an instrument shaft with a large cross-section requires a larger access port and a larger incision. Therefore, what is needed is a tissue fastening instrument and tissue fastener having a shaft with a reduced cross-section capable of reaching surgical sites through smaller access ports and smaller incisions.

SUMMARY OF THE INVENTION

A method for applying a surgical fastener including the steps of providing a fastener applier having an elongated shaft with at least one fastener located within the elongated shaft. The fastener has a pair of bosses extending laterally therefrom. The fastener has an open and closed position. The method further includes the step of inserting the distal end of the shaft into a target location within a body of a patient. Thereafter, the method includes applying at least one fastener within a body of a patient. This step involves the steps of advancing the at least one fastener within the shaft so it is adjacent the distal end, placing the fastener in contact with tissue, and closing the fastener by moving the bosses away from each other as the fastener is advanced distally.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 12 is a cross-section view of the device showing the shaft assembly, pushing mechanism, and fastener transforming from the open to closed position into tissue during further distal movement into the bend channels.

FIG. 13 is a cross-section view of the device showing the shaft assembly and the fastener after it has been transformed into the closed position around tissue.

DETAILED DESCRIPTION OF THE INVENTION

Figure 1:
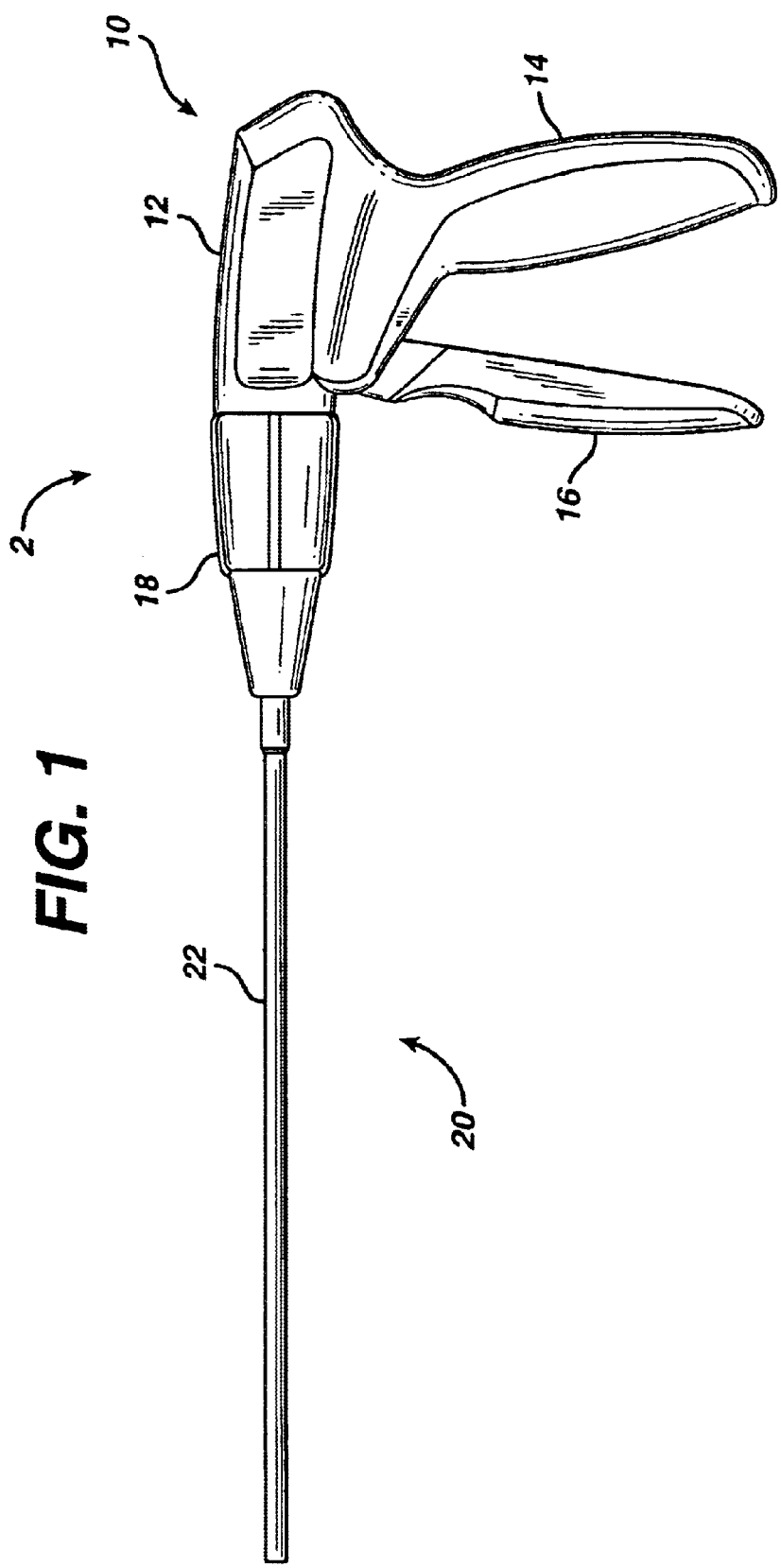
FIG. 1 is a perspective view of the fastener device of the present invention.

Reference numerals are used in this description to designate the various components and elements of the instrument of this invention. Identical reference numerals designated in the various drawings refer to the identical element or component of the surgical penetration instrument. As used in this description, "proximal" or "proximally" refers to that portion of the instrument, component, or element which extends toward the user. Conversely, "distal" or "distally" refers to that portion of the instrument, component, or element which extends away from the user.

Referring to FIG. 1, there is shown fastener device 2, which includes shaft assembly 20 and housing assembly 10, of the present invention. Housing assembly 10 includes housing 12 and handle 14. Housing 12, which may be made from a suitable, rigid medical grade thermoplastic such as, for example, polypropylene or polycarbonate, is integrally attached to handle 14 forming generally a pistol shape. Housing 12, which has a cavity therein, comprises feeding mechanism. Feeding mechanisms are well known in the art and one of many suitable materials such as, for example, springs, may be selected for use in feeding mechanism. Housing assembly 10 further includes trigger 16, which could be comprised of many suitable materials known in the art most of which are rigid thermoplastics such as, for example, polycarbonate. Trigger 16 extends from housing 12 and is pivotally mounted thereto. Attached to the distal end of housing 12 is the proximal end of knob 18. Knob 18, which is preferably made of a rigid polymer such as, for example, polycarbonate, is generally conical having a cavity therethrough. Knob 18 permits 360 degree rotation of shaft assembly 20 with respect to housing assembly 10.

Figure 2:
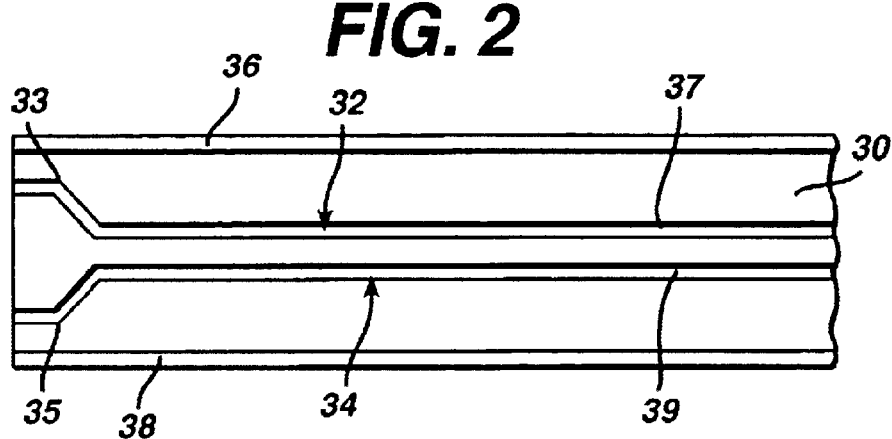
FIG. 2 is section view of the shaft assembly of the present invention illustrating the surface in connection with the shaft.
Figure 3:
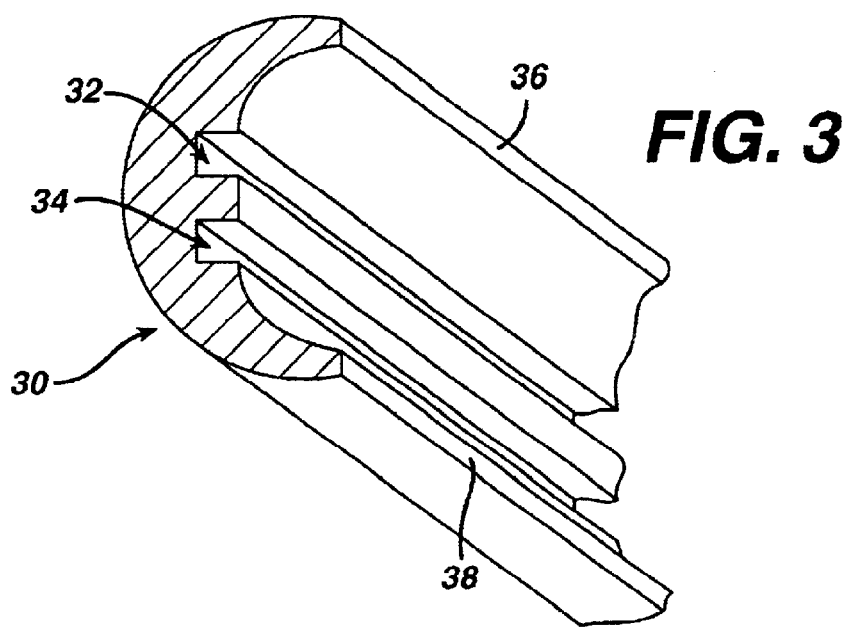
FIG. 3 is a perspective view of the surface in the shaft assembly of the present invention including the first and second channels.
Figure 4:
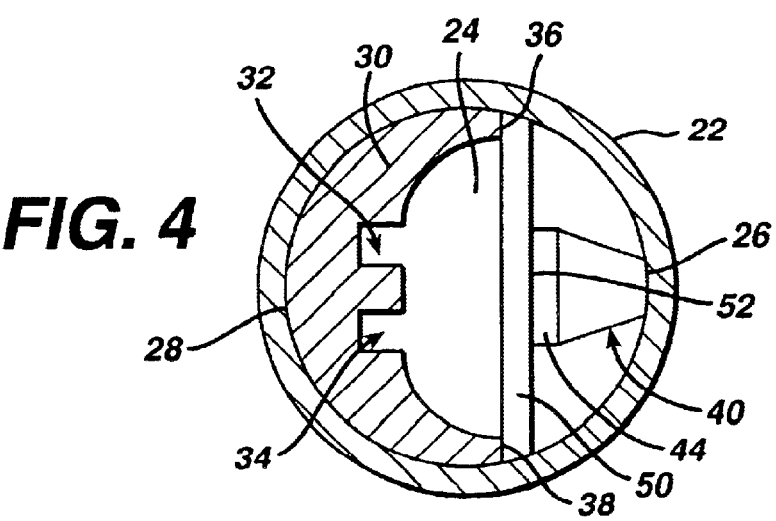
FIG. 4 is an end view of the distal end of shaft assembly of the present invention.

As illustrated in FIGS. 2, 3, and 4, shaft assembly 20 comprises shaft 22, surface 30, pushing mechanism 40, and retaining wall 50. Shaft 22, which is preferably made of a reinforcing material such as, for example, stainless steel, aluminum or any other material known to those skilled in the art, is generally a tubular structure having a proximal end and a distal end. Shaft 22 has cavity 24 therethrough created by its inner diameter which forms first sidewall 26 and second sidewall 28. Attached to second sidewall 28 of shaft 22 is surface 30, as shown in FIG. 4. Surface 30 is generally a semi-tubular structure made from a rigid polymer such as, for example, polycarbonate, or any other material known to those skilled in the art. Surface 30 has first channel 32 and second channel 34 extending generally longitudinal therein. First channel 32 and second channel 34 are integrally molded from surface 30 using manufacturing methods such as, for example, injection molding.

Referring to FIG. 2, first channel 32 and second channel 34 include first straightaway 37 and second straightaway 39 which extend parallel to the longitudinal axis of shaft 22. First channel 32 and second channel 34 further includes first bend channel 33 and second bend channel 35. First bend channel 33 is integrally attached to the distal end of first straightaway 37. Second bend channel 35 is integrally attached to the distal end of second straightaway 39. First bend channel 33 and second bend channel 35 fan away from the longitudinal axis at the distal end of surface 30. Surface 30 further includes first wall 36 and second wall 38. Attached to first wall 36 and second wall 38 of surface 30 is retaining wall 50 as shown in FIG. 4. Retaining wall 50, which is generally an elongated rectangular structure made from a rigid polymer such as, for example, polycarbonate, or any other material known to those skilled in the art, extends longitudinally through shaft 22. Retaining wall 50 includes retaining side 52. Biased against retaining side 52 of retaining wall 50 is pushing mechanism 40. Pushing mechanism 40 is generally an elongated structure preferably formed from a single piece of thin, resilient material such as, for example, stainless steel or any other material known to those skilled in the art. Pushing mechanism 40, which extends longitudinally through shaft 22 and out its proximal end, has a bend at the distal end to form pushing arm 42. Located at the distal end of pushing arm 42 is pushing wall 44, which will be described in more detail later.

Figure 5A:
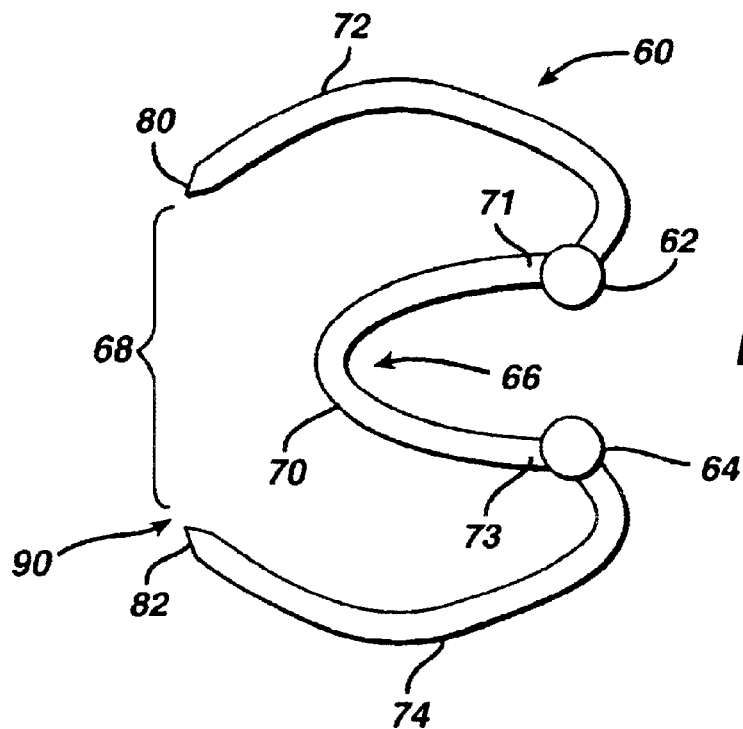
FIG. 5A is a section view of the fastener of the present invention illustrating the open position.
Figure 5B:
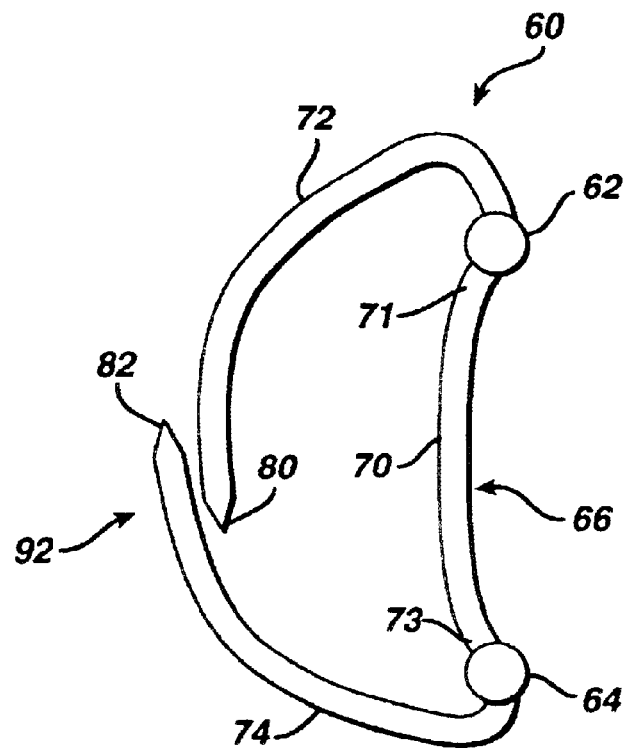
FIG. 5B is a section view of the fastener of the present invention illustrating the closed position.

Referring to FIG. 5A and FIG. 5B, there is shown fastener 60 of the present invention. Fastener 60, which is preferably made of a ductile bio-compatible metal such as, for example, titanium or tantalum, includes first boss 62 and second boss 64 extending laterally therefrom. First boss 62 and second boss 64 generally have circular cross-sections and are integrally attached to fastener 60. Fastener 60 further comprises closed end 66 and open end 68. Open end 68 is adjacent to distal end 23 of shaft 22 when the fastener 60 is being deployed. Closed end 66 has connecting member 70 therebetween. Connecting member 70, which is generally curved, comprises first end 71 and second end 73. First end 71 may be integrally or separately attached to the distal end of first boss 62. Second end 73 is integrally attached to the distal end of second boss 64. Closed end 66 includes first elongated leg 72 extending longitudinally therefrom. First elongated leg 72 is generally curved having a distal end and a proximal end. The proximal end of first elongated leg 72 may be integrally or separately attached to the proximal end of first boss 62. The distal end of first elongated leg 72 includes first tip 80, which is generally conical and sharp to facilitate fastening tissue. Closed end 66 further comprises second elongated leg 74 extending longitudinally therefrom. Second elongated leg 74 is generally curved having a distal end and a proximal end. The proximal end of second elongated leg 74 is integrally attached to the proximal end of second boss 64. The distal end of second elongated leg 74 comprises second tip 82, which is generally conical and sharp to facilitate fastening tissue. Fastener 60 has open position 90 and closed position 92. Open position 90 of fastener 60 is generally W shaped as shown in FIG. 5A. Closed position 92 of fastener 60 is generally box shaped as shown in FIG. 5B. Open position 90 and closed position 92 will be described in more detail later.

Figure 6:
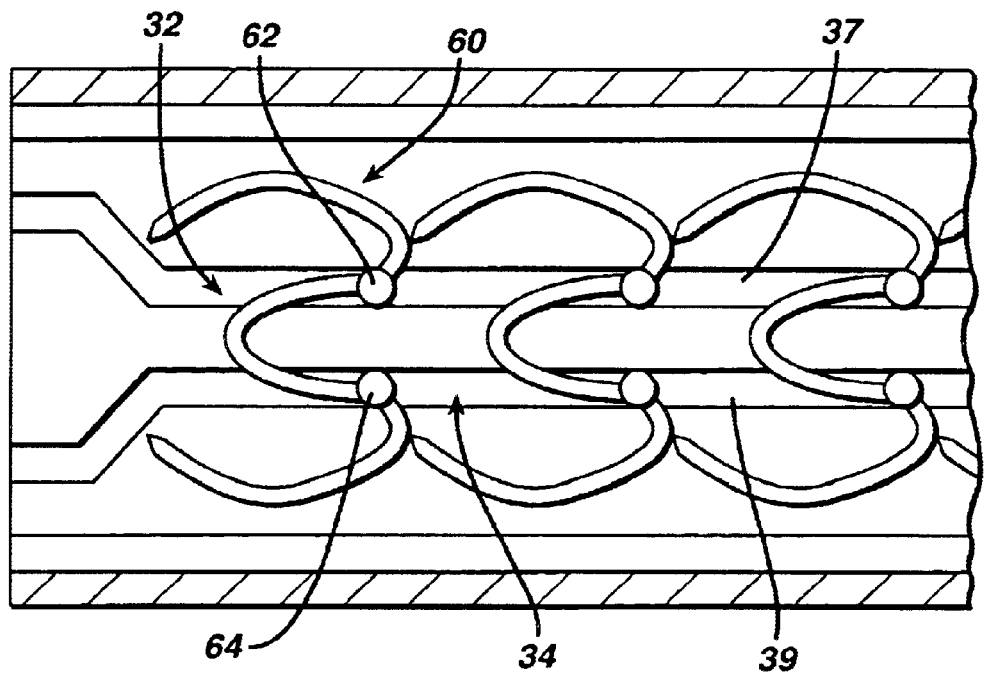
FIG. 6 is a section view of the shaft assembly of the present invention illustrating how the fasteners are assembled into the surface.

Referring now to FIG. 6, it can be understood how fastener 60 is assembled into shaft assembly 20. First boss 62 and second boss 64 are slid into the proximal ends of first straightaway 37 of first channel 32 and second straightaway 39 of second channel 34 respectively such that first boss 62 resides in first channel 32 and second boss 64 resides in second channel 34. Fastener 60 is then moved distally in surface 30 and stopped prior to coming in contact with first bend channel 33 and second bend channel 35. A series of fasteners 60 can then be slid into first channel 32 and second channel 34 such that the first tip and second tip of each fastener is positioned against the closed end of the fastener distal to it in the series.

Shaft assembly 20, including fastener 60, is assembled to housing assembly 10 forming fastener device 2 of the present invention. Pushing mechanism 40 which extends longitudinally within and out of the proximal end of shaft 22 is fixedly attached to trigger 16 such that when trigger 16 is actuated pushing mechanism 40 moves distally beyond retaining wall 50. The distal end of the feeding mechanism would be biased against closed end 66 of the proximal most fastener 60 of a series of fasteners 60. The distal end of knob 18 which has a cavity therethrough is coupled to the proximal end of shaft assembly 20.

Figure 7:
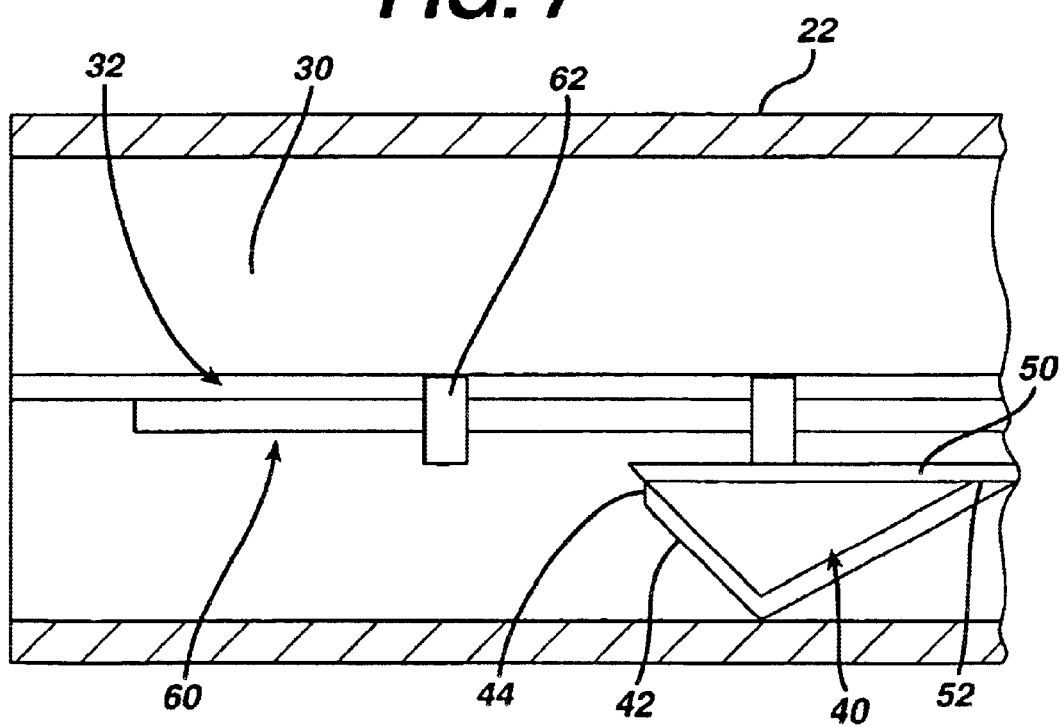
FIG. 7 is a top perspective view of the shaft assembly showing the pushing mechanism resting against the retaining wall prior to actuating the trigger.
Figure 8:
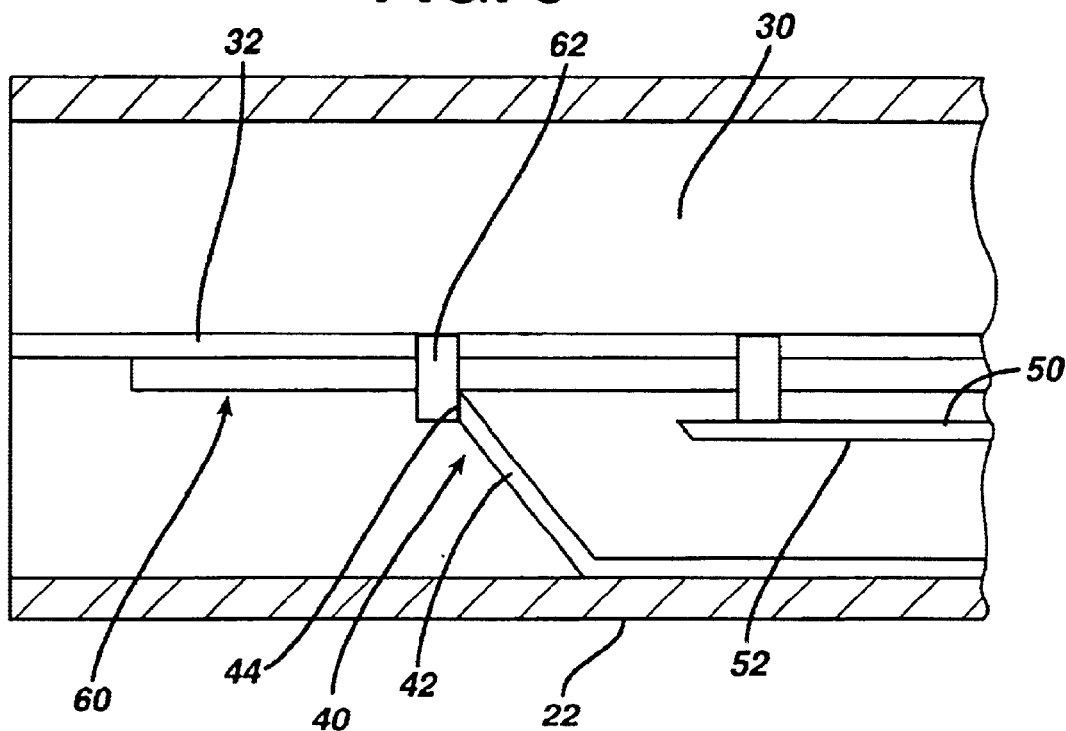
FIG. 8 is a top perspective view of the shaft assembly showing the pushing mechanism biased against the distal most fastener after actuating the trigger.
Figure 9:
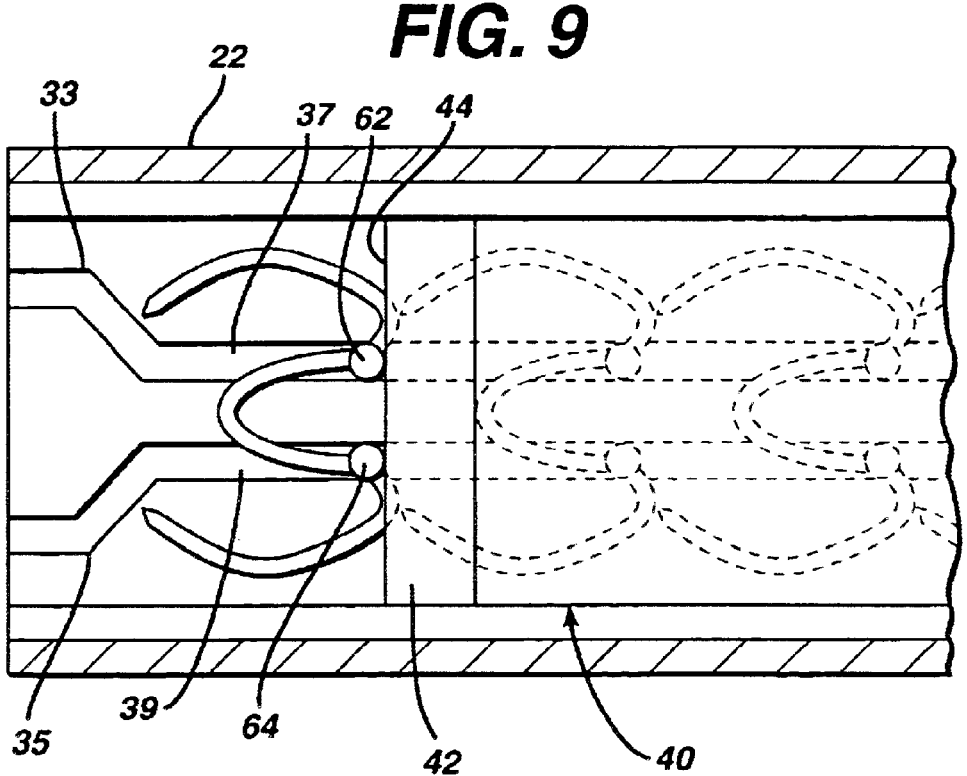
FIG. 9 is a cross-section view of the device showing the shaft assembly and pushing mechanism advancing the fastener distally.
Figure 10:
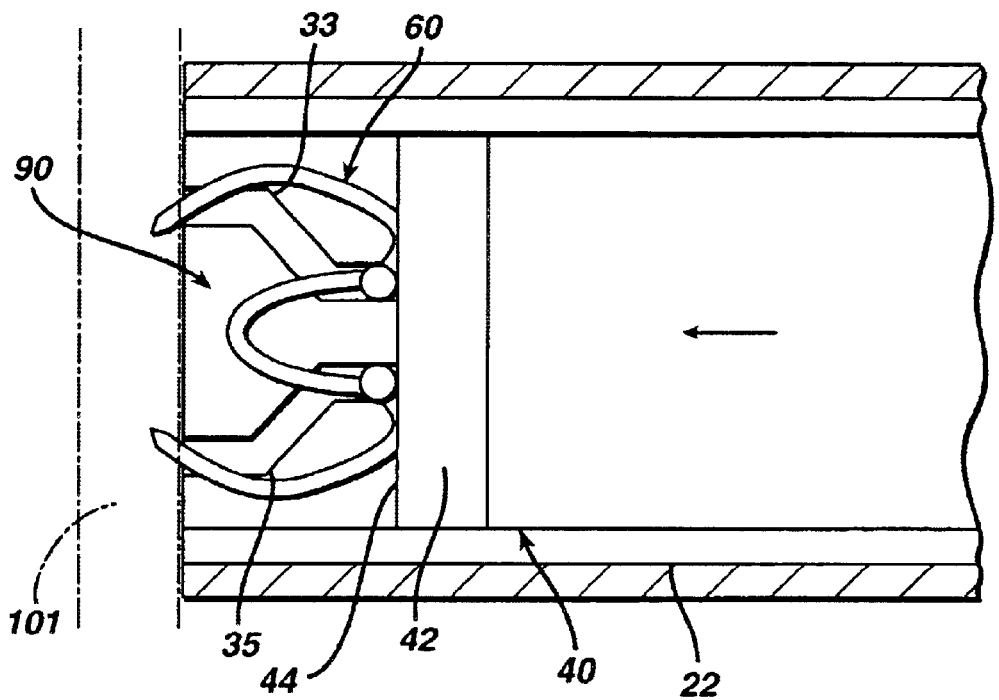
FIG. 10 is a cross-section view of the device showing the shaft assembly and pushing mechanism advancing the fastener distally into the bend channels.
Figure 11:
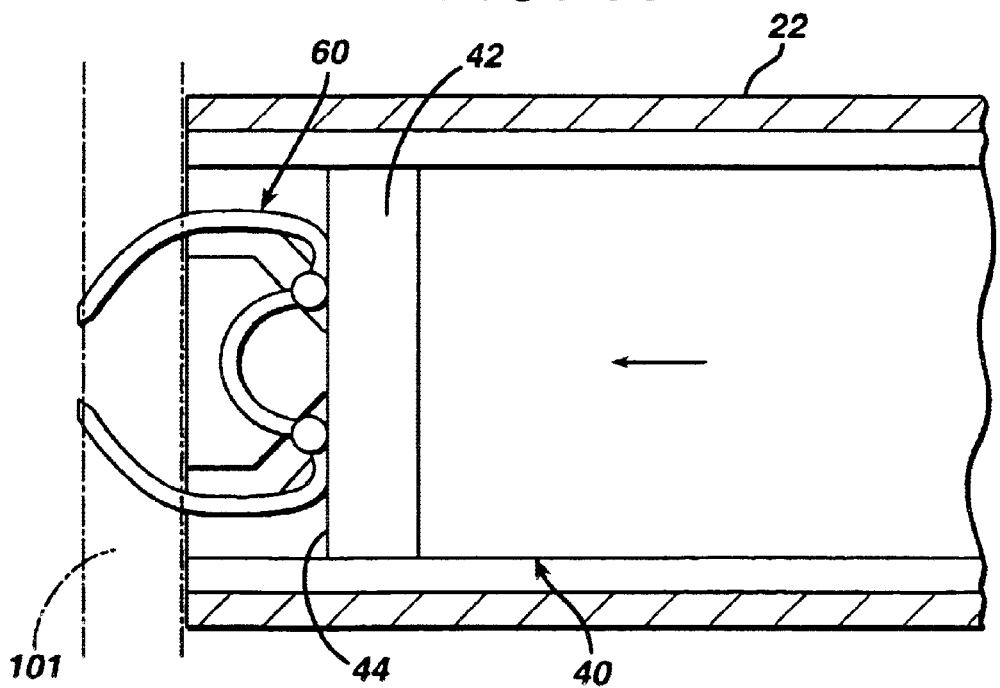
FIG. 11 is a cross-section view of the device showing the shaft assembly, pushing mechanism, and fastener transforming from the open to closed position into tissue during distal movement into the bend channels.

FIGS. 7–13 show an endoscopic or laparoscopic procedure utilizing fastener device 2 of the present invention. After gaining access to the surgical site through, for example, a trocar, the surgeon inserts fastener device 2 through the access way to the surgical site such that segments of body tissue 101 to be joined are placed against the distal end of shaft assembly 20. Knob 18 is rotated to allow the surgeon to get the proper orientation of the fastener at the target location. After positioning fastener device 2 at the target location, the surgeon grasping handle 14 of housing assembly 10 actuates trigger 16. During actuation, pushing mechanism 40, which is fixedly attached to trigger 16, is propelled past retaining wall 50 as shown in FIGS. 7 and 8. After propelling past retaining wall 50, pushing wall 44 of pushing mechanism 40 is biased against the proximal end of first boss 62 and second boss 64 of the distal most fastener 60 in shaft 22. The surgeon then releases trigger 16. During the release of trigger 16, pushing mechanism 40 advances the distal most fastener 60 past first straightaway 37 and second straightaway 39 and into first bend 33 and second bend 35 respectively as shown in FIGS. 10 and 11. Fastener 60 is continually advanced distally through first bend 33 and second bend 35. During the distal movement through first bend 33 and second bend 35, fastener 60 begins to be transformed from open position 90 to closed position 92 shown by FIGS. 11 and 12. When the trigger is completely released, fastener 60 is advanced out of the distal end of shaft 22 completely transforming into closed position 92. As shown in FIG. 13, closed position 92 of fastener 60 fastens segments of body tissue 101 which are placed against the distal end of shaft 22.

Figure 14:
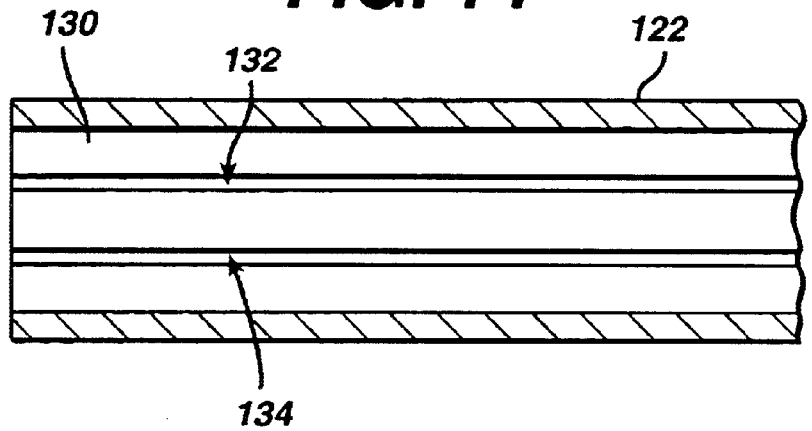
FIG. 14 is a section view of an alternate embodiment of the surface of the present invention connected to the shaft.
Figure 15A:
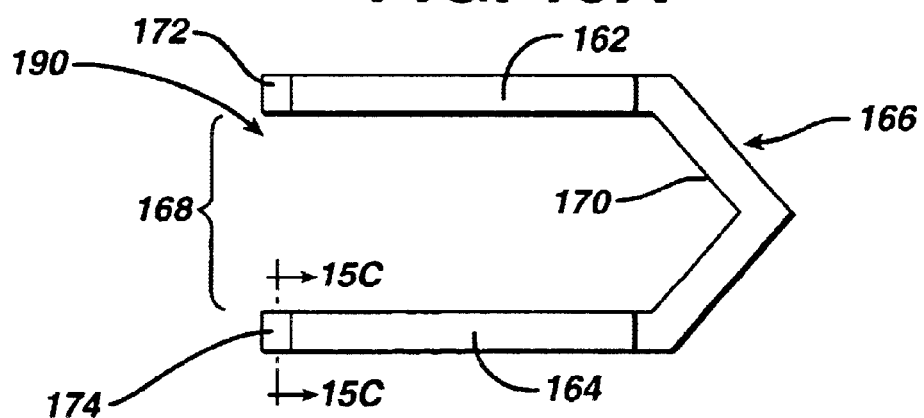
FIG. 15A is a perspective view of an alternate embodiment of the fastener of the present invention illustrating the open position.
Figure 15B:
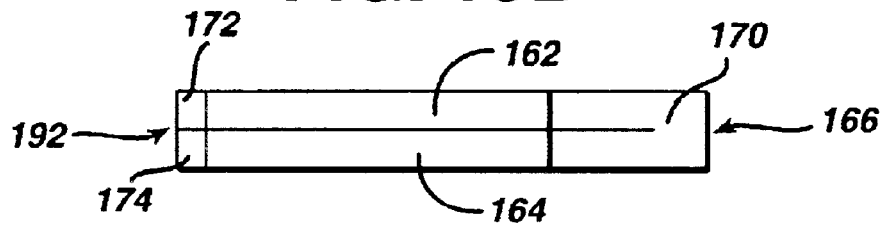
FIG. 15B is a perspective view of an alternate embodiment of the fastener of the present invention illustrating the closed position.
Figure 15C:
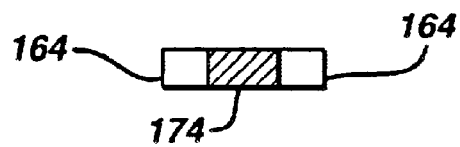
FIG. 15C is an end view of an alternate embodiment of the fastener of the present invention taken along line 15C—15C of FIG. 15A.
Figure 16:
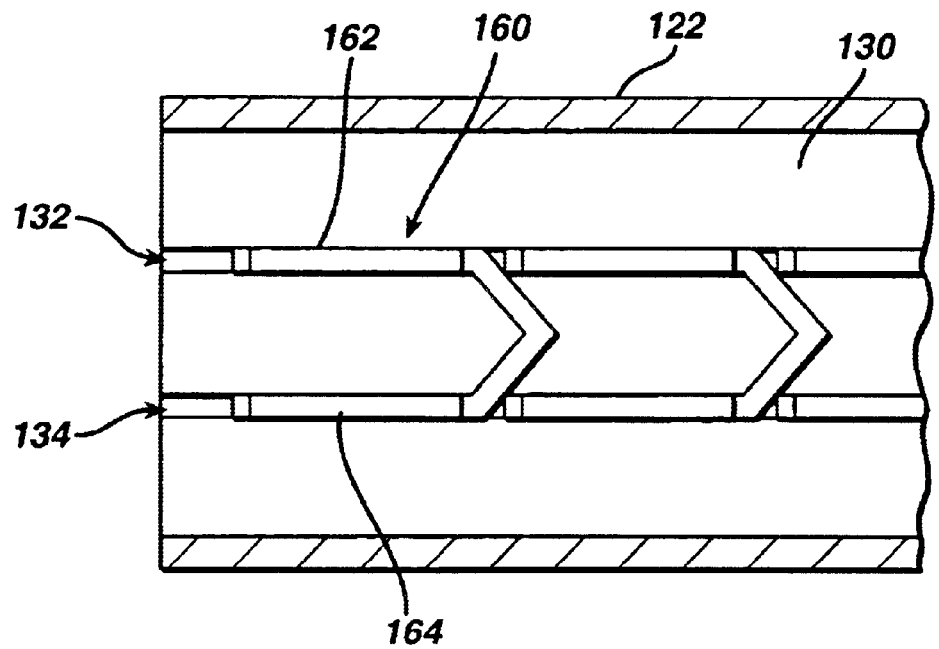
FIG. 16 is a section view of an alternate embodiment of the shaft assembly of the present invention illustrating how the fasteners are assembled into the surface.
Figure 17:
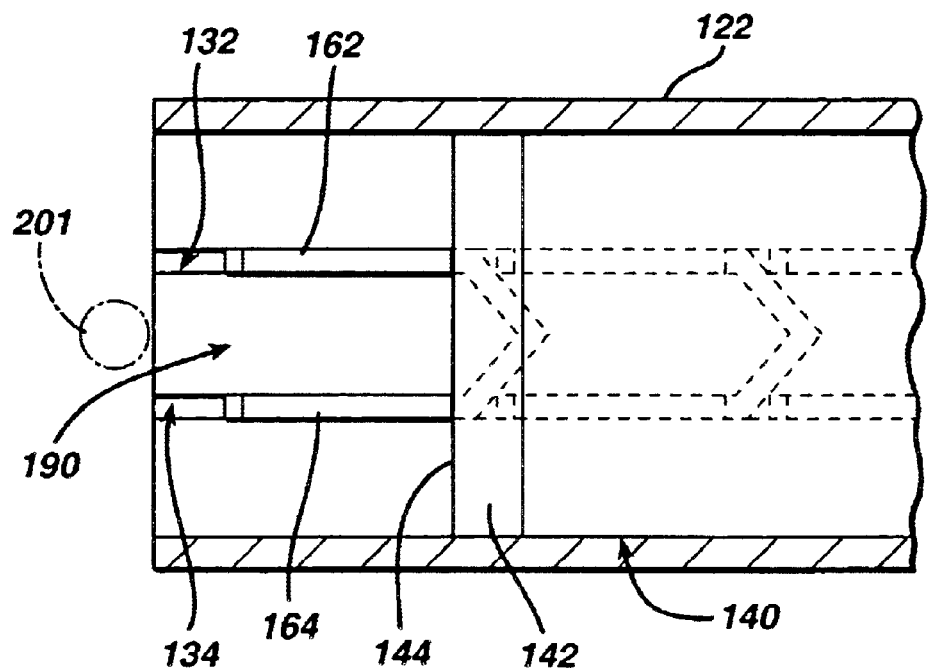
FIG. 17 is a cross-section view of an alternate embodiment of the device showing the shaft assembly and pushing mechanism advancing the fastener distally.
Figure 18:
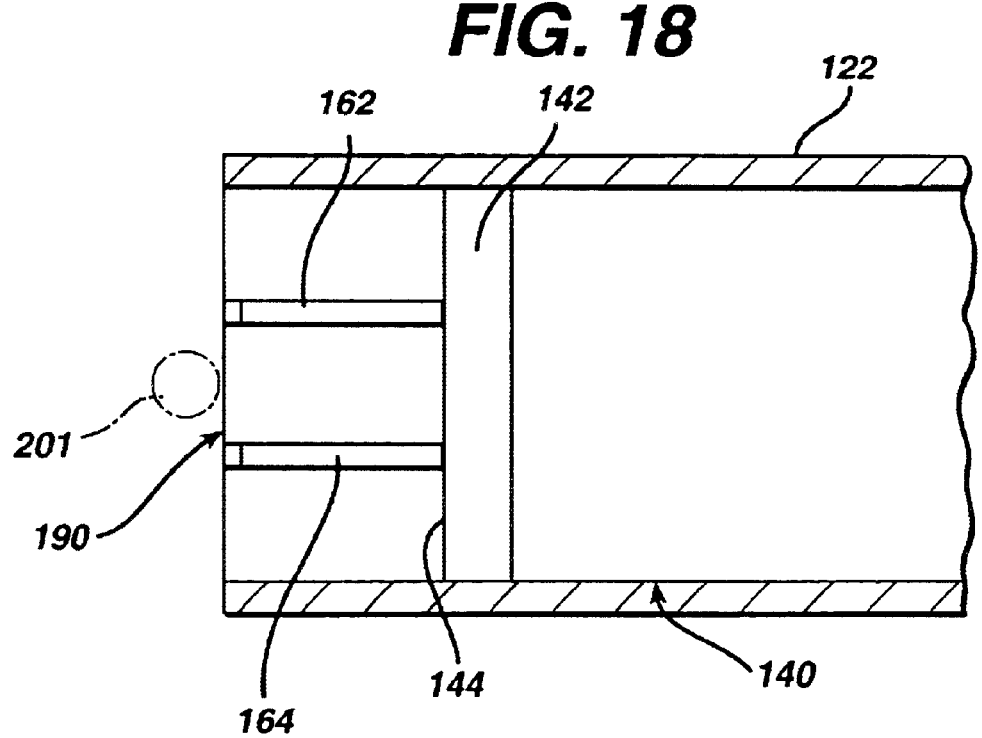
FIG. 18 is a cross-section view of an alternate embodiment of the device showing the shaft assembly and pushing mechanism further advancing the fastener distally.
Figure 19:
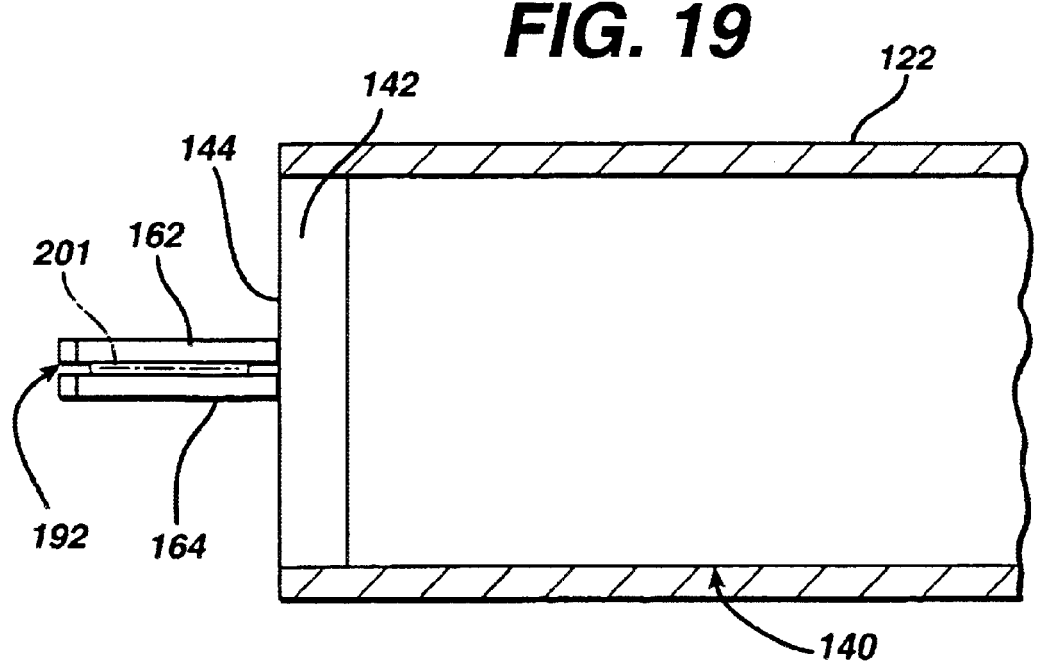
FIG. 19 is a cross-section view of an alternate embodiment of the device showing the shaft assembly and the fastener after it has been removed out of the shaft and transformed into the closed position around a vessel.

Referring to FIGS. 14–19, there is shown an alternate embodiment of the fastener device 102 of the present invention including fastener 160 and surface 130. As shown in FIGS. 15A–15C, fastener 160, which is preferably made of a spring-like bio-compatible metal such as, for example, Nitinol, includes first boss 162 and second boss 164 extending laterally therefrom. First boss 162 and second boss 164 generally have elongated rectangular cross-sections are integrally attached to fastener 160. Fastener 160 further comprises closed end 166 and open end 168. Open end 168 is adjacent to distal end 123 of shaft 122. Closed end 166 has connecting member 170 therebetween. Connecting member 170, which is generally V-shaped, comprises first end 171 and second end 173. First end 171 is integrally attached to the proximal end of first boss 162. Second end 173 is integrally attached to the proximal end of second boss 164. Closed end 166 includes first elongated leg 172 extending longitudinally therefrom. First elongated leg 172 is generally straight having a distal end and a proximal end. The proximal end of first elongated leg 172 is integrally attached to the distal end of first boss 162. Closed end 166 further comprises second elongated leg 174 extending longitudinally therefrom. Second elongated leg 174 is generally straight having a distal end and a proximal end. The proximal end of second elongated leg 174 is integrally attached to the distal end of second boss 164. Fastener 160 has open position 190 and closed position 192. Open position 190 of fastener 160 is generally V-shaped as shown in FIG. 15A. Closed position 192 of fastener 160 is generally U-shaped as shown in FIG. 15B. Fastener 160 begins in closed position 192 and is retained in open position 190 by first boss 162 residing in first channel 132 and second boss 164 residing in second channel 134 of surface 130 as shown in FIG. 14. Surface 130 is generally a semi-tubular structure made from a rigid polymer such as, for example, polycarbonate, or any other material known to those skilled in the art. Surface 30, as shown in FIG. 16, comprises first channel 132 and second channel 134. First channel 132 and second channel 134, which are generally straight, extend longitudinally from the distal end of shaft 122 to the proximal end of shaft 122 running parallel to the longitudinal axis. First channel 132 and second channel 134 are integrally molded from surface 130 using manufacturing methods such as, for example, injection molding. FIGS. 17–19 show an endoscopic or laparoscopic procedure utilizing the alternate embodiment of fastener device 2 of the present invention. In the procedure, fastener 160 is retained in open position 190 by first boss 162 residing in first channel 132 and second boss 164 residing in second channel 134. After pushing mechanism 140 moves fastener 160 out of distal end 123 of shaft 122, fastener 160 closes around vessel 201 and returns to closed position 192.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A method for applying a surgical fastener, said method comprising:
   a. providing a fastener applier comprising an elongated shaft having a distal and proximal end, at least one fastener located within said elongated shaft, said fastener having a pair of bosses extending laterally therefrom, said fastener having an open and closed position;
   b. inserting said distal end of shaft into a target location within a body of a patient; and
   c. applying at least one fastener within a body of a patient comprising the steps of:
      i. advancing said at least one fastener within said shaft so it is adjacent said distal end and placing said fastener in contact with tissue; and
      ii. closing said fastener by moving said bosses away from each other as said fastener is advanced distally.

* * * * *